United States Patent [19]

Konishi et al.

[11] Patent Number: 4,837,018

[45] Date of Patent: Jun. 6, 1989

[54] VACCINES FOR FOWL COLIBACILLOSIS

[75] Inventors: Takao Konishi, Ikeda; Giichi Sugimori, Ayama; Kazuyoshi Kato, Fuchu; Nobutake Kimura, Irima; Kenji Shibata, Kawagoe, all of Japan

[73] Assignees: Shionogi & Co., Ltd., Osaka; Nisshin Flour Milling Co., Ltd., Tokyo, both of Japan

[21] Appl. No.: 79,803

[22] Filed: Jul. 31, 1987

[30] Foreign Application Priority Data

Aug. 13, 1986 [JP] Japan .................................. 61-191119

[51] Int. Cl.$^4$ .................. A61K 39/108; A61K 39/116
[52] U.S. Cl. ......................................... 424/92; 424/93; 435/849
[58] Field of Search ...................... 424/92, 93; 435/849

[56] References Cited

U.S. PATENT DOCUMENTS 4,298,597 11/1981 Acrps et al. ........................ 424/92

FOREIGN PATENT DOCUMENTS 58-131920 6/1983 Japan .

Primary Examiner—Howard E. Schain
Attorney, Agent, or Firm—Wenderoth, Lind & Ponack

[57] ABSTRACT

A vaccine useful for the protection of poultry from colibacillosis infections which comprises as an active ingredient pre-inactivated and ultrasonicated *E. coli* cells, and a method for protecting poultry from colibacillosis infections which comprises inoculating said vaccine into poultry through cloaca.

2 Claims, No Drawings

VACCINES FOR FOWL COLIBACILLOSIS

This invention relates to a vaccine useful for the protection of poultry from colibacillosis infections. More specifically, this invention relates to a vaccine which comprises as an active ingredient ultrasonically disintegrated cells of *Escherichia coli* which have been pre-inactivated. This invention also relates to a method for protecting poultry from colibacillosis infections which comprises inoculating the vaccine of the invention into the poultry through cloaca.

"Fowl colibacillosis" includes various diseases in poultry caused by pathogenic *E. coli* strains (colibacillus), such as colisepsis, arrthritis, hemorrhagic enterisis, and the like. Mass outbreak of colisepsis in broilers, among others, brings serious economical damage to farmers. Accordingly, development of any efficient method for the treatment and prophylaxis of the fowl colibacillosis has long been a major problem to poultry farmers.

Chemotherapeutics and antibiotics have been hitherto used therefor. However, the value of these medicines is now decreasing because of the appearance of resistant strains. Therefore, in place of these medicines, a vaccine useful for the protection of poultry from colibacillosis infections has been developed. Thus, vaccine for colibacillosis which comprises whole cells of inactivated *E. coli* has already been known. However, this inactivated vaccine is not only highly toxic, but also less effective in protecting poultry from colibacillosis infections.

On the other hand, it has already been suggested that toxicity of the inactivated vaccine and appearance of resistant strains can be reduced when the vaccine is inoculated into poultry through cloaca (Japanese Patent Publication (unexamined) No. 131920/1983).

It has now been found that prophylactic activity of inactivated *E. coli* cells is significantly increased when the inactivated cells are ultrasonically disrupted, and that such pre-inactivated and ultrasonicated *E. coli* cells have desirable properties for use in vaccines to be employed for the treatment and prophylaxis of colibacillosis infections in poultry. It has also been found that the vaccine prepared as such shows less toxicity when administered through cloaca as previously suggested.

Accordingly, in one aspect, this invention provides a vaccine useful for the protection of poultry from colibacillosis infections which comprises *E. coli* cells which have been pre-inactivated and ultrasonicated.

This invention also provides a method for protecting poultry from colibacillosis infections by inoculating the vaccine into poultry through cloaca.

As use herein, "pre-inactivated *E. coli* cells" means *E. coli* cells which have been inactivated in usual ways.

"Pre-inactivated and ultrasonicated *E. coli* cells" refers to *E. coli* cells which have been subjected to an inactivating process and then to an ultrasonic disruption process.

"Poultry" refers to domestic fowls such as chickens, ducks, quails, pigeons, turkeys, and the like.

DETAILED DESCRIPTION OF THE INVENTION AND PREFERRED EMBODIMENT

Preparation of pre-inactivated E. coli cells

Pathogenic *E. coli* cells are isolated from organs (e.g. air sac) or droppings of poultry suffering from colibacillosis and grown in a culture medium by conventional methods. The resulting cell culture is treated by an inactivating agent such as formalin (a 40% aqueous formaldehyde solution), phenol, acetone, alcohols, and the like. As will be understood to those skilled in the art, any other known inactivating methods, for example, lyophilisation and heat treatment can also be used.

Preparation of pre-inactivated and ultrasonicated E. coli cells

The inactivated cell culture prepared above is subjected to an ultrasonic disruption treatment using any commercially available apparatus (e.g. Cell Disruper 200, BRANSON) under appropriate conditions. Suitable conditions for the disruption treatment may vary depending on the particular apparatus and other factors. When Cell Disruper 200 is employed, the ultrasonic disruption may be conducted under the following conditions: maximum output, 50% oscillation frequency, for 5 minutes, three times, with cooling on ice. Any other ultrasonicating apparatus can be used for preparing the vaccine of the invention, provided that such apparatus can successfully injure and destroy *E. coli* cells.

Alternatively, the inactivated cell culture may be first centrifuged to collect the cells, which are then suspended in PBS to prepare a bacterial solution. The resulting bacterial solution is then subjected to the ultrasonic disruption treatment as mentioned above.

Vaccine preparation

A process for the preparation of vaccines which contain inactivated bacteria cells as an active ingredient is well known to the art. The vaccine of the present invention which contains pre-inactivated and ultrasonicated *E. coli* cells can be prepared in the same manner as the known vaccines.

The vaccine of the invention may contain an adjuvant, for example, an aluminum compound such as aluminium hydroxide gel, or Freund's complete adjuvant. The vaccine of the invention may also contain a preservative for prevention of the growth of undesirable microorganisms. Preferred preservatives are, for example, marzonine, tyrosine, benzoic acid, formaldehyde solution, salicylic acid, crystal violet, surfactants such as benzetonium chloride, polymyxin, gramicidine, and the like.

The vaccine of the invention can be conventionally administered, for example, intramuscularly, intravenously, or subcutaneously. However, such administration routes may sometimes cause weight loss of poultry as in the case of known vaccines. However, such disadvantageous effect can be reduced or diminished by inoculating the vaccine through cloaca as stated before. Typically, 0.002–0.2mil (about $2 \times 10^5 - 2 \times 10^{10}$ CFU/ml) of vaccine of the invention is inoculated through cloaca into each poultry such as chicken, duck, or turkey. Such doses are sufficient to protect the poultry from colibacillosis and to prevent mass infections of said disease.

The following examples are provided to further illustrate and exemplify the present invention.

Example 1

(1) Vaccine (1)

Pathogenic *E. coli* strains ($O_2$) isolated from air sacs of chickens suffering from colibacillosis were incubated in a broth medium at 37° C. for about 24 hours. To the cell culture was added formalin to a final concentration of 0.2%. The inactivated cell culture thus obtained contained more than $1.5 \times 10^9$ cells per ml (CFU/ml). A portion of the cell culture was ultrasonicated using Cell Disruper 200 (BRANSON) at 50% oscillation frequency under maximum output (5 minutes, 3 times) with cooling on ice. This gave vaccine (1) of the invention.

(2) Vaccine (2)

Inactivated cells were collected by centrifugation ($14000 \times G$ for 20 minutes at 4° C.), and then suspended into PBS to prepare a bacterial solution which contained inactivated *E. coli* cells at a density of $2 \times 10^{10}$ CFU/ml. The bacterial solution was then applied to the aforementioned Cell Disruper to yield vaccine (2) of the invention.

The PBS solution was prepared as follows: 11.9g of $NaH_2P_4$ $12H_2O$, 3.6g of $NaH_2PO_4$ $2H_2O$, and 0.6g of NaCl were throughly admixed. To the mixture was added distilled water to a final volume of 1 liter, and the resultant solution was sterilized before use.

The vaccines prepared above were inoculated into poultries, and the immunization activity thereof was evaluated as descried below.

Experiment

Pathogenic *E. coli* solution and its inactivated solution prepared in Examples (1,1) and (1,2) were used as positive control vaccine (1) and positive control vaccine (2) respectively. Eleven chicks (Chankey, broiler species) within 30 hours after hatching were used for tests. Each chick was inoculated with 0.03ml of vaccine (1), vaccine (2), positive control vaccine (1) or positive control vaccine (2) through cloaca by intravenous drip method (see Japanese Patent Publication (unexamined) No. 131920/1983). When the chick become 21-days-old, $6 \times 10^7$ CFU of pathogenic *E. coli* cells, the same strain as used in the preparation of the vaccines, were intravenously injected into each chick. Another group of 12 chicks received only the pathogenic *E. coli* cells, which served as a negative control. Prophylactic action of the vaccines was evaluated on the basis of the number of survivals on the seventh day after infection, and survival rates were statistically analyzed using $\chi^2$ test. The results are shown below in Table 1.

TABLE 1

| | Immunization Effect of Vaccine (1) and Vaccine (2) | | | | | | | | |
|---|---|---|---|---|---|---|---|---|---|
| | Number of Chicks Tested | Number of Dead Animals After Infection | | | | | | Number of Survivals (Survival Rate) | $\chi^2$ Test |
| | | 1 | 2 | 3 | 4 | 5 | 6 | 7 | |
| | | (Days After Infection) | | | | | | | |
| Negative control | 12 | 7 | 2 | 1 | 0 | 0 | 0 | 0 | 2 (16.7) | — |
| Vaccine (1) | 11 | 2 | 1 | 1 | 0 | 0 | 0 | 0 | 7 (63.6) | * |
| Positive control vaccine (1) | 11 | 4 | 1 | 1 | 0 | 0 | 0 | 0 | 5 (45.5) | |
| Vaccine (2) | 11 | 0 | 0 | 0 | 1 | 0 | 0 | 0 | 10 (90.9) | ** |
| Positive control vaccine (2) | 11 | 0 | 3 | 2 | 1 | 0 | 0 | 0 | 5 (45.5) | |

*$P < 0.05$ (statistically significant)
**$P < 0.01$ (statistically significant)

The table shows that the vaccines of the invention exhibit remarkable prophylactic action when compared with the conventional vaccines.

What is claimed is:

1. A vaccine useful for the protection of poultry from colibacillosis infection, which comprises as an active ingredient ultrasonically disintegrated cells of *E. coli* which have been pre-inactivated.

2. A method for protecting poultry from colibacillosis infections, which comprises inoculating the vaccine of claim 1 into poultry through cloaca.

* * * * *